United States Patent [19]

Highgate et al.

[11] Patent Number: 4,768,503

[45] Date of Patent: Sep. 6, 1988

[54] POLYMERIC COMPOSITION

[75] Inventors: Donald J. Highgate, Whaddon; John D. Frankland, Dartford, both of England

[73] Assignee: Eschmann Bros. & Walsh Limited, London, England

[21] Appl. No.: 761,562

[22] Filed: Aug. 1, 1985

Related U.S. Application Data

[63] Continuation of Ser. No. 464,908, Feb. 8, 1983, abandoned, which is a continuation of Ser. No. 274,398, Jun. 17, 1981, abandoned, which is a continuation of Ser. No. 119,518, Feb. 7, 1980, abandoned.

[30] Foreign Application Priority Data

Feb. 8, 1979 [GB] United Kingdom ................ 7904485

[51] Int. Cl.[4] ............................................. A61L 15/00
[52] U.S. Cl. ..................................... 128/156; 604/336
[58] Field of Search ............................... 128/355–356, 128/155, 156; 106/129, 173.1; 604/33 G; 526/260

[56] References Cited

U.S. PATENT DOCUMENTS

| | | | |
|---|---|---|---|
| 2,927,868 | 3/1960 | Revoir | 428/356 |
| 3,339,546 | 9/1967 | Chen | 128/156 |
| 3,532,679 | 10/1970 | Steckler | 526/260 |
| 3,877,431 | 4/1975 | Kross | 604/336 |
| 3,980,084 | 9/1976 | Kross | 604/336 |
| 4,078,568 | 3/1978 | Etez et al. | 604/336 |
| 4,166,051 | 8/1979 | Cilento et al. | 604/336 |
| 4,192,785 | 3/1980 | Chen et al. | 604/336 |
| 4,204,540 | 5/1980 | Cilento et al. | 604/336 |
| 4,231,369 | 11/1980 | Sorensen et al. | 604/336 |
| 4,421,822 | 12/1983 | Levens | 428/355 |

Primary Examiner—C. Fred Rosenbaum
Assistant Examiner—Mark F. Colosimo
Attorney, Agent, or Firm—McAulay, Fields, Fisher, Goldstein & Nissen

[57] ABSTRACT

A polymeric composition is disclosed which has sealant and preferably also adhesive properties and which is suitable for use as a protective dressing for application to the skin. The composition comprises a chemically cross-linked hydrophilic polymer and a support matrix such as a high molecular weight hydrophobic polymer. The hydrophilic polymer is a water-swellable polymer which absorbs or adsorbs water but which is water-insoluble. The composition preferably includes a tackifyer which may be provided by a low molecular weight fraction of a hydrophobic matrix or by a distinct adhesive component such as a gum or a low molecular weight polymer. The composition is particularly suitable for use as a sealing ring in conjunction with a post-surgical drainage appliance wherein the hydrophilic polymer is incorporated in a form such as to provide a transmission system for liquid.

8 Claims, No Drawings

POLYMERIC COMPOSITION

This is a continuation of application Ser. No. 464,908 now abandoned, filed Feb. 8, 1983; which was a continuation of Ser. No. 274,398 now abandoned, filed June 17, 1981, which was a continuation of Ser. No. 119,518 now abandoned, filed Feb. 7, 1980.

This invention relates to a polymeric composition and, in particular, to a polymeric composition having sealant properties, and preferably also adhesive properties, and which is suitable for application to the skin.

According to a particular embodiment, the present invention provides a polymeric composition for use as a protective dressing in the form for example, of a ring which is suitable for use as a sealant, preferably also having adhesive properties, with, for example, a drainage bag or pouch which is worn by patients after surgical operation.

Certain surgical operations, e.g. colostomy, ileostomy and urinary diversion, result in the formation of an opening, known as a stoma, in the abdominal wall. A reliable seal between the skin of the patient and an ostomy appliance, such as a drainage bag or pouch, is essential in order, inter alia, to prevent leakage and/or irritation of the skin.

Similarly, drainage bags or pouches are worn by patients to drain faecal fistulae, urinary fistulae and in conjunction with post-surgical body cavity drainage. In all cases an effective seal between the skin of the patient and the drainage bag or pouch is required.

One material which has been commonly used to protect the skin, particularly in conjunction with an ostomy appliance, is a semi-gelatinous ring of the naturally occuring hydrocolloid, Karaya, obtained from tree-sap and normally used together with an oleaginous, non-evaporative carrier such as glycerol. There are, however, certain problems associated with the use for this purpose of Karaya. One problem is that conventional ostomy rings of Karaya have a limited life since, when they have absorbed a significant amount of water, the rings lose their shape and strength. There exists, therefore, a need for a protective dressing which avoids the problems associated with the use of conventional Karaya-based materials.

Various materials have been proposed as substitutes for the naturally occuring Karaya, in particular for use with ostomy appliances. However, in general, these materials contain a hydrocolloid and/or a water-soluble polymer and it has been found that these materials lose much of their strength when the hydrocolloid has absorbed a significant quantity of water and, thus, are readily disturbed by movement of the ostomy appliance.

We have, therefore, attempted to provide an improved polymeric composition suitable for use as a protective dressing which is capable of absorbing water, while retaining its shape and strength over a long period of time.

We have now found, in accordance with the present invention, that these criteria are met by a polymeric composition which comprises at least one chemically cross-linked, hydrophilic polymer and a support matrix.

The term "hydrophilic polymer" is used herein to mean a water-swellable polymer which absorbs or adsorbs water but which is water-insoluble. The chemically cross-linked, hydrophilic polymer is preferably one which has the ability to absorb and/or adsorb between 10% and 90% of water, expressed in terms of the weight of water absorbed/adsorbed as a percentage of the weight of water absorbed/adsorbed plus the weight of dry polymer.

The support matrix may be, for example, a hydrocolloid, a water-soluble polymer, a hydrophobic polymer or a mixture of these.

We have found that the polymeric composition according to the invention comprising a hydrophilic polymer will only absorb and/or adsorb a finite amount of water and even when the maximum amount of water has been absorbed and/or adsorbed the polymer still retains its original shape and much of its strength and will not disintegrate. This is in contrast to the use of a hydrocolloid and/or water soluble polymer which continues to absorb water to such an extent that it has no residual strength and will ultimately disintegrate and/or dissolve.

This property, inter alia makes the polymeric composition according to the invention very suitable for use as a protective dressing for application to the skin. According to one embodiment the protective dressing may be used in the form of a ring as previously described.

Thus, the present invention also provides a sealing ring for use with a post-surgical drainage appliance comprising a bag or pouch adapted to receive drainage from the body of a patient via a stoma, fistula, lesion or the like, the ring having an opening to permit the ring to surround the stoma, fistula, lesion or the like thereby forming a seal between the skin of the patient and the drainage appliance and which ring is formed from a polymeric composition comprising a matrix and at least one chemically crosslinked, hydrophilic polymer which is incorporated in the composition in a form such as to provide a suitable transmission system for liquid as herein defined.

By the phrase "suitable transmission system for liquid" we mean that, in use in conjunction with a drainage appliance, the sealing ring has good liquid permeability normal to the skin i.e. normal to the plane of the ring and very low permeability transverse to the skin i.e. transverse to the plane of the ring. By means of the present invention it is possible to have substantially zero permeability transverse to the skin at the inner edge of the sealing ring which can increase towards the outer periphery.

According to another aspect of the invention the composition is provided in the form of a solid sheet for subsequent adaptation to ring-form as just described or as a protective dressing for skin lesions, varicose ulcers, pressure sores and the like. According to another embodiment the protective dressing may be employed as a means of retaining an appliance or appendage to the skin e.g. for securing a male incontinence sheath to the penis.

The ring or sheet of the polymeric composition according to the invention may be provided as part of a drainage appliance, such as an ostomy appliance or it may be provided for subsequent adaptation for use with a particular drainage appliance or it may be provided as a dressing.

According to a further aspect, the composition according to the invention is provided in the form of a paste, gel, or liquid including a volatile carrier. The composition in paste-, gel- or liquid-form can be applied to the skin and thereafter the carrier is evaporated to leave a film of similar composition to that of the solid ring or sheet previously described.

According to one aspect of the present invention the polymeric composition according to the invention may be suitable for use as a protective dressing simply having sealant properties without any adhesive properties and it has been found that it is sometimes desirable to separate these functions. In the case where, for example, the dressing is in the form of a sealing ring used in conjunction with a drainage bag or pouch then a separate adhesive material or a mechanical securing aid would be employed.

According to this aspect of the invention, the polymeric composition may comprise the hydrophilic polymer together with a matrix comprising a high molecular weight hydrophobic polymer such as a polyolefin, especially polyisobutylene having a viscosity average ($M\overline{v}(S)$) molecular weight of between 120,000 and 130,000. Alternatively the hydrophilic polymer may be used together with a matrix comprising a water-soluble material.

However, according to a preferred aspect of the present invention, the polymeric composition has both sealant and adhesive properties and is thus particularly suitable for use as a protective dressing suitable for application to the skin, optionally in conjunction with an appliance such as an ostomy appliance.

Thus, according to a particular embodiment, the invention provides a polymeric composition comprising at least one high molecular weight hydrophobic polymer; and at least one chemically cross-linked, hydrophilic polymer, the polymeric composition including a tackifier which can be provided by a low molecular weight fraction of the high molecular weight, hydrophobic polymer and/or by a distinct component preferably comprising a low molecular weight polymer.

The high molecular weight, hydrophobic polymer component acts as a skeleton or backbone to hold the composition together and to give it sufficient mechanical strength.

In general, the viscosity average molecular weight (Staudinger) ($M\overline{v}(S)$) of the hydrophobic polymer is at least 100,000, preferably from 100,000 to 150,000.

According to one embodiment, the hydrophobic polymer includes a tackifier fraction. In this case, the hydrophobic polymer should include at least 5% and preferably at least 10% of a fraction having a high molecular weight and at least 10% of a fraction having a low molecular weight. The high molecular weight fraction provides the backbone of the composition and gives its strength, as just described, and the low molecular weight fraction provides a sufficient degree of tackiness such that the composition will adhere to skin under its own weight.

According to an alternative embodiment, the tackifier is provided by a distinct component or mixture of components, which is preferably a low molecular weight polymer, preferably a hydrophobic polymer, and which is also preferably derived from the same monomer as that from which the high molecular weight, hydrophobic polymer is derived. The low molecular weight polymer provides a sufficient tackiness to adhere the composition to the skin. The low molecular weight polymer preferably has a molecular weight ($M\overline{v}(S)$) of between 200 and 30,000.

As a further possibility the adhesive component may be or may be augmented by for example, a water-activated adhesive or a non-aqueous, single or two-component adhesive.

According to another embodiment of the invention a polymeric composition having sealant and adhesive properties comprises the hydrophilic polymer, and optionally a high molecular weight hydrophobic polymer and optionally a tackifier, together with a water-activated adhesive such as karaya. By this means, the advantages of the widely used known material would be combined with the advantages arising from the use of the hydrophilic polymer according to this invention.

The hydrophilic polymer can also be used in conjunction with a matrix containing a hydrocolloid or a water-soluble material to improve adhesive properties when the composition is used in a situation where substantial amounts of water are present.

In general, the composition according to the invention comprises at least 10% by weight, based on the weight of the total composition, of the at least one chemically cross-linked, hydrophilic polymer and preferably from 30 to 70% by weight. According to a particular embodiment, the composition comprises about 60% by weight, based on the weight of the total composition, of the chemically cross-linked, hydrophilic polymer or polymers. However, within these preferred limits a hydrocolloid may replace a portion of the hydrophilic polymer.

The ratio of the proportion of the high molecular weight hydrophobic polymer relative to the low molecular weight tackifier polymer or to the low molecular weight fraction of the hydrophobic polymer is preferably in the range of 1:1 to 1:5 by weight and in particular approximately 1:3 by weight. However, where, as preferred, the tackifier is hydrophobic, and where the composition contains a relatively small proportion, i.e. towards the lower preferred limit of 10%, of the hydrophilic polymer, then the composition should include a microporous or water-permeable filler for example, Talc or chalk. The presence of the filler reduces the proportion of the hydrophobic material present and hence maintains the hydraulic permeability of the composition.

The polymeric composition according to the invention may optionally also include one or more other ingredients, for example, medicaments, deodorants and pH controllers.

Further details of the components of the polymeric compositions according to the invention are given in the following.

The chemically cross-linked, hydrophilic polymer may be, for example, a homopolymer of a hydrophilic monomer, for example, a vinyl lactam, such as N-vinyl pyrrolidone; a hydroxy-alkyl acrylate or methacrylate e.g. hydroxyethyl methacrylate; acrylamide and methacrylamide and N-substituted derivatives thereof or a copolymer of two or more of these hydrophilic monomers. Suitable N-substituted derivatives include mono- and di-substituted compounds having alkyl, hydroxyalkyl and aminoalkyl groups e.g. N-methyl acrylamide, N-isopropylacrylamide N,N-dimethyl acrylamide, N,N-dimethylaminoethyl acrylamide and N-methylaminoisopropylacrylamide. The chemically cross-linked hydrophilic polymer may also be a copolymer of a hydrophilic monomer, as just exemplified, with a hydrophobic comonomer such as an alkyl or aminoalkyl acrylate or methacrylate, e.g. methyl methacrylate or acrylonitril or methacrylonitrile.

The preferred hydrophilic polymer is a copolymer of methyl methacrylate and N-vinyl pyrrolidone. This polymer may be prepared by polymerization using radiation or a chemical agent, in the presence of a chemical cross-linking agent such as a diolefinically unsaturated cross-linking agent e.g. allyl methacrylate or an acrylate or methacrylate of a polyhydroxy alcohol.

The matrix may comprise a high molecular weight, hydrophobic polymer, for example, a polyolefin such as a polyisobutylene, a natural or synthetic rubber such as polyurethane rubber, a silicon rubber, a polyisoprene rubber or a mixture of these polymers. The preferred high molecular weight, hydrophobic polymer is a polyisobutylene having a viscosity average ($M\bar{v}(S)$) molecular weight of between 120,000 and 130,000 e.g. a commercially available product called Vistanex (Trade mark)L140. Most preferably this constitutes approximately 10% by weight of the total composition.

The low molecular weight polymer which acts as a tackifyer in one embodiment of the composition according to the invention is preferably a polyisobutylene having a molecular weight ($M\bar{v}(S)$) within the range of 6,000 to 20,000 and a viscosity within the range of 180,000 to 220,000 SSU at 98.9° C. Such a material is exemplified by the commercially available products Hyvis (Trade mark) 2000, and Vistanex LM-MS and LM-MH grades. It is most preferred for this low molecular weight polymer to constitute approximately 30% by weight of the total composition.

Where the tackifyer is provided by a low molecular weight fraction of the high molecular weight polyisobutylene, at least 10% of the polyisobutylene should have a molecular weight ($M\bar{v}(S)$) of greater than 100,000 and at least 10% of the polyisobutylene should have a molecular weight ($M\bar{v}(S)$) of less than 30,000.

According to a preferred embodiment of the invention the composition comprises approximately 10% by weight of a polyisobutylene having a molecular weight ($M\bar{v}(S)$) of between 120,000 and 130,000; approximately 30% by weight of a polyisobutylene having a molecular weight ($M\bar{v}(S)$) within the range of 6,000 to 20,000 and a viscosity within the range of 180,000 to 220,000 SSU at 98.9° C.; and 60% by weight of a chemically cross-linked copolymer of methyl methacrylate and N-vinyl pyrrolidone, all percentages being based on the total weight of the composition. A portion of the hydrophilic polymer in this preferred composition may be replaced by a hydrocolloid or a water-soluble polymer. For example the composition may contain 30 to 40% by weight of the hydrophilic polymer together with 20 to 30% by weight of a hydrocolloid such as karaya.

The function of the hydrophilic polymer in a polymeric composition applied as a protective dressing to the skin may be two-fold. First, the hydrophilic polymer may act as a reservoir for liquid, e.g. perspiration, from the surface of the skin, and second, the hydrophilic polymer may also act as a transmission system, that is a direct path for the liquid from the skin to the atmosphere. These functions render the composition particularly suitable for use in skin care and especially for use as a sealant with drainage bags or pouches such as those used in ostomy appliances.

In order to fulfil the second function of providing a suitable transmission system for liquid, the hydrophilic polymer may be incorporated in various forms in the composition, such as granules, filaments or hollow fibres.

Referring to the use of the polymeric composition as a sealing ring according to the invention, in a first embodiment the hydrophilic material may be incorporated in the form of granules at low average volume concentrations with the density of the granules being controlled such that, at least in a part of the composition, the granules provide a path for moisture. For example, the granules may be incorporated with a higher concentration at the outer periphery of the sealing ring. In this embodiment, particle-particle contact may allow transmission at the outer edge without seepage from the stoma.

Another possibility is to incorporate the hydrophilic polymer as granules at high average volume concentrations relative to the hydrophobic content, e.g. approximately 60%. In this embodiment, reservoir and transmission effects will occur by particle-particle contact, and some additional means of sealing the edge at the stoma will be required.

Alternatively, according to a second embodiment the hydrophilic polymer may be incorporated as filaments passing through the system normal to the skin. This system automatically provides high permeability normal to the skin and low permeability around the stoma. In a refinement of this arrangement the hydrophilic polymer is incorporated as filaments (as just described) but of variable volume concentration increasing toward the outer surface or otherwise directed within the material.

Another, although less preferred, possibility may be adopted where the hydrophilic polymer has relatively low permeability. This involves the use of hollow fibres or filaments of the hydrophilic polymer to provide selective directional transmission of the liquid.

According to the first embodiment of the invention, the hydrophilic polymer is employed in granular form either in a proportion or an arrangement which ensures that there exists a path for liquid from the skin to the atmosphere.

In this system, the composition desirably includes a water-soluble adhesive, The adhesive may be incorporated into the composition in dry form e.g. by milling and can be activated in situ by moisture from the skin. Therefore, the hydrophilic polymer also acts as a slow release vehicle for the tackifier whereby the adhesive component or components are released due to uptake of water by the hydrophilic polymer. The adhesive properties are thereby maintained over a long period of time.

According to the second embodiment of the invention, permeability normal to the skin is controlled independently from the other properties of the polymeric composition by the use of filaments of the hydrophilic material which are arranged to extend through the thickness of the sealing ring thereby providing a direct path for liquid from the skin to the atmosphere. Hollow fibres or filaments of the hydrophilic material may be similarly arranged. According to a particular aspect, the density of the hydrophilic fibres or filaments is controlled such that their density, and hence liquid permeability normal to the skin, increases towards the outer periphery of the sealing ring.

In this system the composition desirably includes a non-aqueous adhesive or, preferably, an aqueous adhesive. Where an aqueous, or water-soluble adhesive is employed the adhesive may conveniently be incorporated into the polymeric composition in dry form e.g. by milling. The adhesive is activated in situ by moisture from the skin which is transmitted via the hydrophilic polymer.

The hydrophilic material may also act as a release system for other optional components of the composition such as medicaments, pH controllers and deodorants.

That is, the hydrophilic material controls the rate of release of the adhesive component or components according to the rate of uptake of water from the skin by the hydrophilic material. By this means the hydrophilic material can act as a slow release system for the adhesive whereby the adhesive characteristics are maintained over a long period of time.

In both systems just described it may be desirable, in order to assist in inhibition of transverse permeability of liquid from the stoma, to provide a means for sealing the centre of the sealing ring. This could be effected, for example by introducing an impermeable layer of plastics material, such as polythene, during production of the sealing ring or by subsequent application of a coating. It is desirable to obtain a sealing ring wherein the percentage by volume of the hydrophilic polymer may increase from substantially zero at the inner edge of the ring to about 60% at the outer periphery.

An anisotropic material suitable for use as a sealing ring may be produced, for example from two or more compositions comprising the matrix such as a hydrophobic material with different concentrations of the hydrophilic material in granular form. The different compositions could be co-extruded; pressed from a central unit of a composition having a low concentration of hydrophilic granules and a ring of a composition having a high concentration of hydrophilic granules; or pressed into separate flat sheets and rolled together, one on top of the other, with the discs being cut from a cross section of the resulting roll. Alternatively an anisotropic material may be produced by aligning filaments of the hydrophilic polymer and injecting the hydrophobic material around them; the desired product could then be sliced off from the stock rod thus obtained.

In order to prepare an isotropic composition according to the present invention the hydrophilic polymer, preferably in a finely ground state, may be dispersed, for example by milling, in the matrix. The matrix may be premixed with an adhesive component or with any optional components of the polymeric composition optionally in the presence of a solvent e.g. normal hexane or perchloroethylene, which is subsequently removed. Another possibility is to feed the essential components into a high shear mixer.

We have found that the composition according to the present invention has particularly good properties which make it suitable for use with drainage appliances such as ostomy appliances. Thus, the composition has the important advantage that it is readily flexible, hence accommodating movement of the patient, while being liable to less flow, than, for example, previous compositions incorporating a hydrocolloid. In addition, the composition according to this invention does not readily support bacterial growth and conveniently, the composition may be sterilised. The composition according to the present invention has a longer life since it is capable of absorbing water while maintaining its shape and strength; in contrast to compositions in which the water-absorption capacity is provided by hydrocolloids. Finally the composition according to the present invention is a more effective sealant and allows the skin to remain in a healthy condition by allowing removal of moisture from the skin while maintaining access of gases to the skin.

The invention is illustrated by the following Examples.

EXAMPLE 1

Vistanex L140 (80 g) is cut into small lumps and fed gradually into a high shear Z-blade mixer loaded with Hyvis 2000 (240 g). Finely ground methyl methacrylate-N-vinyl pyrrolidone co-polymer (480 g) is then also added gradually to the mix the co-polymer having a particle size of 106–500 microns. Mixing is continued until a homogeneous material is obtained (total mixing time approx. 45 mins.). The mixer is then unloaded and the product pressed into sheets of the desired thickness which are subsequently cut into the required shape.

EXAMPLE 2

Vistanex L140 (88.8 g) is cut into small lumps and fed gradually into a high shear Z-blade mixer loaded with Hyvis 2000 (80 g). Methyl methacrylate-N-vinyl pyrrolidone co-polymer (272 g) (having the same particle size as in Example 1) is then added slowly, and the mixer run for a further 30 mins. to give a homogeneous material. A further quantity of Hyvis 2000 (151 g) is then added followed by mixing for a further 5 mins. Karaya powder (208 g) is then added, with mixing for another 5 mins. After checking for homogeneity the product is unloaded from the mixer and pressed and cut as in Example 1.

We claim:
1. A protective dressing suitable for application to the skin which comprises a hydrophilic polymeric composition consisting essentially of
   (i) from 30 to 70 percent by weight of at least one chemically cross-linked hydrophilic polymer selected from the group consisting of:
      (a) homopolymers of hydrophilic monomers selected from the group consisting of vinyl lactams, hydroxy-alkyl acrylates, hydroxy-alkyl methacrylates, acrylamide, methacrylamide, N-substituted derivatives of acrylamide, N-substituted derivatives of methacrylamide;
      (b) copolymers of at least two of the said hydrophilic monomers; and
      (c) copolymers of at least one of the said hydrophilic monomers with at least one hydrophobic monomer
   (ii) a support matrix for the said hydrophilic polymer, wherein the said support matrix comprises at least one hydrophobic polymer having a viscosity average molecular weight of 100,000 to 150,000.
2. A protective dressing according to claim 1, wherein a portion of the said chemically cross-linked hydrophilic polymer is replaced by a hydrocolloid.
3. A protective dressing according to claim 1, wherein the said chemically cross-linked hydrophilic polymer is a copolymer of methyl methacrylate and N-vinyl pyrrolidone.
4. A protective dressing according to claim 1, wherein the said high molecular weight hydrophobic polymer is polyisobutylene having a viscosity average molecular weight of between 120,000 and 130,000.
5. A protective dressing suitable for application to the skin which comprises a polymeric composition consisting essentially of
   (i) at least one chemically cross-linked hydrophilic polymer which is a copolymer of at least one hydrophobic monomer with at least one hydrophilic monomer selected from the group consisting of vinyl lactams, hydroxyalkyl acrylates, hydroxyalkyl methacrylates, acrylamide, methacrylamide,

N-substituted derivatives of acrylamide and N-substituted derivatives of methacrylamide;

(ii) support matrix for the said hydrophilic polymer comprising at least one hydrophobic polymer having a viscosity average molecular weight of 100,000 to 150,000; and (iii) a tackifier comprising a low molecular weight polymer having a viscosity average molecular weight of from 200 to 30,000, said low molecular weight polymer being derived from the same monomer as that from which the hydrophobic polymer of the support matrix is derived.

6. A protective dressing suitable for application to the skin which comprises a polymeric composition consisting essentially of (i) at least one chemically cross-linked hydrophilic polymer which is a copolymer of at least one hydrophobic monomer with at least one hydrophilic monomer selected from the group consisting of vinyl lactams, hydroxyalkyl acrylates, hydroxyalkyl methacrylates, acrylamide, methacrylamide, N-substituted derivatives of acrylamide and N-substituted derivatives of methacrylamide;

(ii) a support matrix for the said hydrophilic polymer comprising at least one hydrophobic polymer having a viscosity average molecular weight of 100,000 to 150,000 and (iii) a tackifier comprising a distinct component or mixture of components having a viscosity average molecular weight of 200 to 30,000.

7. A protective dressing according to claim 6 wherein the support matrix (ii) comprises polyisobutylene having a viscosity average molecular weight of between 120,000 and 130,000 and wherein the tackifier (iii) comprises polyisobutylene having a viscosity average molecular weight within the range of 6,000 and 20,000 and a viscosity within the range of 180,000 to 220,000 SSU at 98.9° C.

8. A sealing ring for use with a post-surgical drainage appliance comprising a bag or pouch adapted to receive drainage from the body of a patient via a stoma, fistula, lesion, or the like, the ring having an opening to permit the ring to surround the stoma, fistula, lesion, or the like thereby forming a seal between the skin of a patient and the drainage appliance and which ring is formed from a protective dressing suitable for application to the skin which comprises a polymeric composition consisting essentially of (i) at least one chemically cross-linked hydrophilic polymer which is a copolymer of at least one hydrophobic monomer with at least one hydrophilic monomer selected from the group consisting of vinyl lactams, hydroxyalkyl acrylates, hydroxyalkyl methacrylates, acrylamide, methacrylamide, N-substituted derivatives of acrylamide and N-substituted derivatives of methacrylamide; and (ii) a support matrix for the said hydrophilic polymer.

* * * * *